United States Patent [19]

Pinsky et al.

[11] Patent Number: 5,317,162
[45] Date of Patent: May 31, 1994

[54] APPARATUS AND METHOD FOR PHASE RESOLVED FLUORESCENCE LIFETIMES OF INDEPENDENT AND VARYING AMPLITUDE PULSES

[75] Inventors: Bertram G. Pinsky, Hayward; Robert A. Hoffman, Livermore, both of Calif.

[73] Assignee: Becton, Dickinson and Company, Franklin Lakes, N.J.

[21] Appl. No.: 941,780

[22] Filed: Sep. 9, 1992

Related U.S. Application Data

[63] Continuation of Ser. No. 705,044, May 23, 1991, abandoned.

[51] Int. Cl.$^5$ ............................................. G01N 21/64
[52] U.S. Cl. .............................. 250/461.2; 250/459.1; 356/317
[58] Field of Search .............. 250/461.2, 458.1, 459.1; 356/318, 417; 436/172

[56] References Cited

U.S. PATENT DOCUMENTS

| | | | |
|---|---|---|---|
| 4,058,732 | 11/1977 | Wieder | 250/461 B |
| 4,198,567 | 4/1980 | Eneroth et al. | 250/459 |
| 4,778,593 | 10/1988 | Yamashita et al. | 209/3.1 |
| 4,840,485 | 6/1989 | Gratton | 250/458.1 |
| 4,855,930 | 8/1989 | Chao et al. | 364/497 |
| 4,910,467 | 3/1990 | Leitch | 329/306 |

OTHER PUBLICATIONS

Berndt et al., "Phase Modulation Fluorometry using a Freq-doubled . . . Laser Diode Source", Rev. Sci. Instrum., 61(7), p. 1816 (1990).
Vo-Dinh et al., "Phase-Resolved Fiber-Optics Fluoroimmunosensor", Applied Spect. 44(1), p. 128 (Jan. 1990).
"Microwave Systems Designer Handbook," Jul., 1987, vol. 17, p. 155.
"Radio Concepts," Ralph S. Carson, pp. 279–282.
Spencer, Richard Dale, 1942, Fluorescence Lifetimes: Theory, Instrumentation, and Application of Nanosecond Fluorometry, University of Illinois at Urbana--Champaign, Ph.D., 1970.
Spencer, Richard D. and Weber, Gregorio, Measurements of Subnanosecond Fluorescence Lifetimes with a Cross–Correlation Phase Fluorometer University of Illinois at Urbana, Ill.

Primary Examiner—Paul M. Dzierzynski
Assistant Examiner—Richard Hanig
Attorney, Agent, or Firm—Aaron Passman; Michael G. Schwarz

[57] ABSTRACT

A flow cytometer measures phase fluorescence lifetimes by the phase shift of a reference signal and an emission from a particle or cell in a flow chamber. An acoustic optic modulator modulates laser light with a sinusoidal wave of a predetermined frequency to excite particles or cells. Detectors respond to emissions of individual particles or cells in the form of an output signal pulse at the predetermined frequency. The output signal pulse is divided into equal pulses with each at the modulation frequency, the same amplitude and fidelity and amplitude. One part of the divided pulse is stripped of its envelope to pass the width thereof and out of band components are rejected. A variable amplifier passes a portion of the pulse above a present level. A delay line sets a central part of the signal at a predetermined point in time. A circuit limits the attenuated one part. A double balance mixer multiplies and the relates the limited signal with a reference signal to determine the phase shift. A method measures phase fluorescence lifetimes of cells or particles with fluorescent markers by passing individual cells or particles in a flow stream of a flow chamber in a flow cytometer.

21 Claims, 8 Drawing Sheets

APPARATUS AND METHOD FOR PHASE RESOLVED FLUORESCENCE LIFETIMES OF INDEPENDENT AND VARYING AMPLITUDE PULSES

This application is a continuation of application Ser. No. 07/705,044, filed May 23, 1991 now abandoned.

1. Field of the Invention

This invention relates to excitation of fluorescently tagged particles with modulated light to obtain fluorescent lifetime by measuring the phase shift of emissions relative to excitations and more specifically, the exponential decay of the emission as a function of the fluorescence and the environment. In particular, lifetime can be used as a separate parameter to distinguish emissions independent of the intensity of the emissions but with similar spectral properties and different decays. In addition any single lifetime emission from a signal of multiple lifetimes may be suppressed through the choice of the reference lifetime.

2. Background

In a flow cytometer, wherein small cells or particles are passed through a light beam at relatively high speed and are tagged with markers or dyes there are a number of issues which are not resolvable by intensity measurements alone. These include; the separation of multiple signals with the similar emission spectra and similar intensity, suppression of a single emitted signal from multiple signals of similar intensity, normalization of intensity varying signals with the same or different fluorescent lifetime and in general the measurement of fluorescent lifetime and all its associated properties.

Fluorescently tagged particles may have multiple fluorescent tags, some having similar emission spectra. Previously the only way to separate these signals with the similar emissions was through intensity differences. If the signals also, have similar intensities then the multiple signals were unresolvable. In contrast, if the signals have different lifetimes and the same or different intensities then they may be resolvable as explained herein.

Fluorescent lifetime is associated with the radiative transition from the fluorescent agents excited state to the that of its relaxed state. The excited state is unique to the fluorescent agent and the fluorescent agent is chosen to be, or is a natural property, representative of a specific property of the cell or particle under observation. The lifetime of the fluorescent agent (fluorochrome) may be determined by phase sensitive or modulation sensitive techniques. The fluorescent lifetime, $\tau$, may be calculated from the measured phase shift relative to a reference signal as follows:

$$\tau = 1/\omega(\mathrm{Tan}\theta)$$

where $$\omega = 2\pi f, \; f = \text{frequency}$$

$$\theta = \text{phase angle}$$

or from the depth of modulation factor m.

$$\tau = 1/\omega(1 m^2 - 1)^{\frac{1}{2}}$$

Fluorescent lifetime is resolved through the measurement of a phase shift by comparison of the fluorescence emission's pulse to a reference signal. The measured signal may include multiple lifetime signals, and therefor multiple phase signals. Since the phase measurement is a relative measurement, the choice of the reference from which the measurement is taken allows for the suppression of any one lifetime emission.

Fluorescent intensity signals may vary over a large range for a single sample having the same physical properties. The phase fluorescence need not depend upon the intensity of the signal. The apparatus and method for applying a phase fluorescence resolution to a high speed and therefore dynamic system is not in the prior technology. Determination of the phase shift between the modulation wave and the modulated emission from the cell or particle is a problem because of the speed at which each cell or particle passes through the flow chamber and the widely varying intensity signal resulting from emissions of fluorescence Fluorescent intensity signals have a signal to noise ratio defined by the overall intensity measured and its associated unwanted fluorescent or scatter background signals and instrument noise., There is in general an optimal excitation intensity for the fluorescently labeled particle where additional excitation intensity only increase the background signal and therefore reduces the signal to noise ratio. Associated with this leveling off of output signal due to increased excitation intensity is a constant fluorescence lifetime distribution. Consequently, it is desirable to exploit the lifetime parameter independent of the intensity variations.

Immunofluorescence is an example where the analysis of signals may be limited by the background fluorescence. This is known as autofluorescence. The sensitivity of the immunofluorescence measurement is limited by the effect of autofluorescence. Although the autofluorescence may have the same spectral emission as the fluorescent tag there may be an associated different fluorescent lifetime with each signal.

The idea of phase detection includes the multiplication of a continuous wave signal of a known amplitude with a signal of interest having the same amplitude and the same frequency. In "Microwave Systems Designer Handbook", July, 1987, vol. 17, page 155, a basic phase detection method appears and is explained. In particular, the method requires a second or reference oscillator, equal in frequency to that of the device under test and if possible, lower in phase noise. The two oscillators feed the input ports of a balanced mixer that has a D.C. coupled output port. If the inputs are of equal frequency and amplitude, the double balanced mixer acts as a phase detector. Its output will be a D.C. voltage proportional to the cosine of the phase angle difference of the two input signals. If the input signals of the double balanced mixer are a continuous oscillator signal and a modulated pulse of significant duration and of the same local oscillator frequency then the peak of the envelope of the output pulse will be representative of the phase.

In a flow cytometer, the intensities of the pulse signals vary largely and measurement of each signal is indirect in that it is a pulse of voltage from a photomultiplier tube indicative of a fluorescent emission and not the direct laser excitation signal. The need to balance the amplitude of each fluorescence emission signal is not known or appreciated in the noted reference. The signals must not be distorted in prefiltering. Variations inherent in the measurements of real samples in a flow cytometer introduce frequency modulation that must be corrected for and the noise should be kept within the duration of the pulse of interest. The preliminary handling of such flow cytometrtic signal from the photomultiplier tube is not suggested, appreciated or disclosed in connection with any known phase detection method.

U.S. Pat. No. 4,778,593 shows that a pico second pulse which results in a decay spread over nanoseconds with a streak camera, can be measured. This arrangement permits low signal strength to be measured at very high cost.

The theory that phase detection in any system having a multiplier of a reference and an input appears in "radio concepts", Ralph S. Carson, pages 279-282. No appreciation of signal modification as required in a flow cytometer is either disclosed or explained since the special handling of the pulses from a photomultiplier tube has not been accomplished in a way which supplies measurable results indicative of characteristics of cells or particles under flow analysis.

In a flow cytometer, multiple populations are frequently considered with detection and measurement of the quantity of each population. Signal enhancement prior to phase detection is required to separate the signals from each population so that a difference in phase shift for each population may be found. Phase detection schemes that were known were used only to detect a single population or pulses from one population.

Normalized signals require that the amplitudes and frequencies that are not of interest are removed without affecting the phase relationship before or after filtering to remove unnecessary signals.

SUMMARY OF THE INVENTION

A flow cytometer measures phase fluorescence lifetimes by determining the phase shift between a reference signal and an emission from a particle or cell passing through a flow chamber of a flow cytometer. The flow chamber is of material transparent to light and positioned in the flow cytometer. The flow chamber may have a passage therethrough. Delivery means in the flow cytometer operates to pass in a stream through the passage individual cells or particles from a population under study.

A source of intensity modulated laser light at a predetermined frequency is positioned to direct the modulated laser light to individual particles or cells passing in the stream through the passage. An acoustic optic modulator may connect to the source to modulate the laser light from the source. Preferably the acoustic optic modulator produces a sinusoidal wave. Detection means responsive to emissions from individual particles or cells illuminated by the source of intensity modulated laser light may generate an output signal at the predetermined frequency. Means divide the output signal into equal signals so each signal is modulated at the modulation frequency and has the same amplitude and fidelity without any amplitude dependent induced phase shift. A high pass filter receives and filters out unneeded portions of one part of the divided signal.

Means reject out of band components of one part of the equally divided signal pulse stripped of its envelope and pass the width thereof. A variable attenuator may set the signal level to a preset level. A delay line may set a central part of the signal at a predetermined point in time. Means responsive to a timing circuit permit the central part of the signal to pass. The means may include a switch responsive to a portion of the other part of the equally divided signal. A comparator controls the switch by comparing the portion and a reference. A limiting circuit may receive and limit an amplified filtered one part of the divided signal. A filter removes from the limited signal harmonics above the modulation frequency and an envelope below a preset level. A double balance mixer multiplies the limited signal with a reference signal and produces a multiple signal thereby relating the reference signal and the filtered limited signal to determine the relative phase shift of the fluorescence emissions.

A reference oscillator may drive the acoustic optic modulator and produce the reference signal used in the double balanced mixer. Means may correlate the measured phase shift to a characteristic of the cells or particles passing through the flow chamber of the flow cytometer. Sorting means may receive the cells or particles and segregate them on the basis of fluorescent lifetimes as determined by phase shift.

A method of measuring in a flow cytometer phase fluorescence lifetimes of cells or particles with one or more fluorescent markers includes passing individual cells or particles in a flow stream through a flow chamber in a flow cytometer. Then each cell or particle passing through the flow chamber is excited with intensity modulated laser light of a wavelength that stimulates at least one of the fluorescence markers. The intensity modulated laser light is preferably at a predetermined modulation frequency. The stimulated fluorescent emissions from the flow chamber may be detected for each cell or particle.

An output signal representative of the detected stimulated emissions may be divided into two equal signals one of which is filtered in a high pass filter. The divided and filtered signal is attenuated and transmitted to a limiting circuit wherein a limited signal may be produced and sent to a double balance mixer. That limited signal with a reference signal are multiplied in the double balance mixer to produce a multiple signal thereby relating the reference signal and the filtered limited signal to determine the relative phase shift of the fluorescence emissions.

The method may have the additional steps of modulating the laser light with an acoustic optic modulator and obtaining a reference signal from a reference oscillator used to drive the acoustic optic modulator which may generate a sinusoidal modulation wave.

The additional step of correlating the measured phase shift to a characteristic of the cells or particles in the stream passing through the flow chamber of the flow cytometer may be practiced. The further step of sorting cells or particles on the basis of fluorescent lifetimes as determined by phase shift is preferred.

DETAILED DESCRIPTION OF THE DRAWINGS

Figure 1:
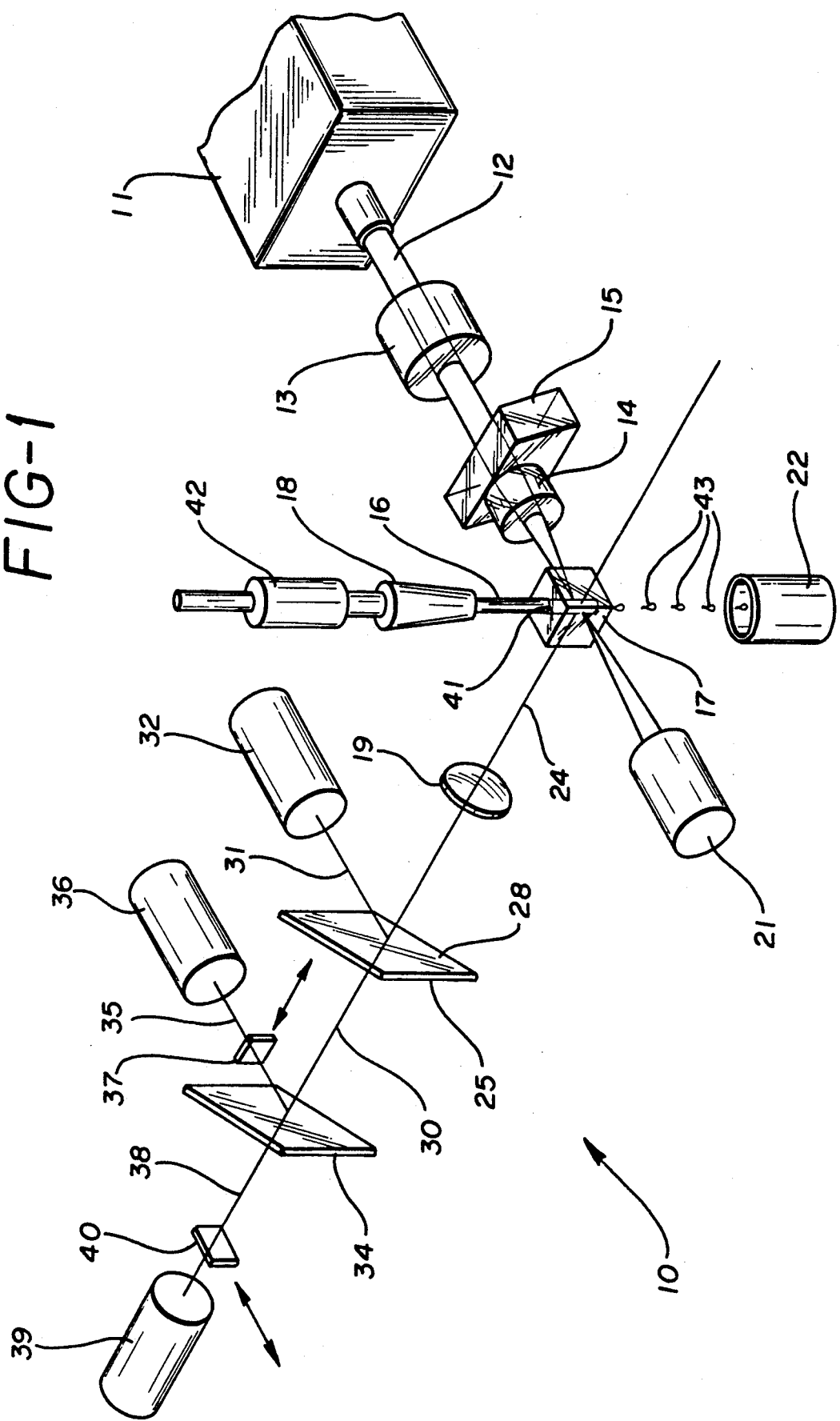
FIG. 1 is a perspective view which is schematic of a flow cytometer apparatus depicting the relationship of the parts thereof and their function.

While this invention is satisfied by embodiments in many different forms, there is shown in the drawings and will herein be described in detail, a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawings, and FIG. 1 in particular, the optical and particle flow elements of a flow cytometry apparatus 10 are illustrated. The optical and flow elements of FIG. 1 represent the major components of a flow cytometry apparatus for moving particles, such as cells or the like, in a liquid streams, substantially one at a time, in order to assess those particles for specific characteristics thereof. For example, the elements of the apparatus of FIG. 1 may be included in a FACS ™ fluorescence-activated cell sorter, manufactured and sold by Becton Dickinson Immunocytometry Systems, San Jose, Calif. The FACS cell sorter analyzes and sorts cell populations on the basis of light scatter and fluorescence in a wide variety of research laboratory applications. In addition to the optical and flow elements to be described in more particular detail herein, and which may be embodied in an instrument such as the FACS cell sorter, other details of a cell sorting apparatus useful in conjunction with the present invention are described in U.S. Pat. No. 3,826,364. It is understood that the present invention is useful in many different types of flow cytometry apparatuses whether measuring light scatter, fluorescence, particle volume or other optical parameters for the identification or quantification of cells or the like in a sample liquid medium. The circuit elements, in particular, of the present invention represent the essence of the improvement in flow cytometry apparatuses such as described in the aforementioned patent.

As illustrated in FIG. 1, light energy is provided for the present flow cytometry apparatus by a light source 11 such as a laser which provides a collimated beam of light at a singular wavelength, or an arc lamp, such as a mercury or xenon arc lamp, which provides an incoherent or non-collimated beam of light comprising a broad spectrum of wavelengths While the laser source 11 may be intensity modulated with an acoustic optic modulator, it may alternatively be intensity modulated with a Pockel, Kerr, De Bye Sears cell, or direct laser diode modulation and appropriate optics and driver electronics.

Excitation energy is provided in flow cytometry apparatus 10 by a beam of light 12 produced by light source 11. It is preferred that laser 11 is model Innova 90 from Coherent Radiation, Palo Alto, Calif. The beam of light passes through an acoustic optic modulator 13, steering optics 15 and then a focusing lens 14 positioned in the optical path of the light stream. Acoustic optic modulator model 3200 from Crystal Technology, Palo Alto, Calif. is used in the preferred embodiment. There are other ways to provide a source of intensity modulated laser light including Kerr cells and Pockel Cells as well as direct modulated laser diodes. The light source does not have to be a laser, for example the SLM Aminco fluorimeter has a mercury arc lamp and a DeBye Sears Cell to modulate the light. Lens 14 focuses the modulated light beam at a liquid stream 16 containing the particles or cells under investigation. In the present flow cytometer apparatus an aperture and steering optics 15 direct the modulated light at a flow chamber 17 which is positioned in the optical path after the lens 14 and the aperture and steering optics 15. Flow chamber 17 of a material transparent to light of the wavelength in the beam 12 is around the liquid flow stream 16. The lens 14 is used to obtain an adjustment of the focused light beam on the liquid stream.

As seen in FIG. 1, a nozzle 18, incorporated within the flow cytometry apparatus of the present invention and preferably as a part of the flow chamber 17, facilitates the flowing of cells or particles within liquid stream 16 through the flow chamber 17. The utilization of nozzle 18 of this type is well-known and is described, for example, in U.S. Pat. No. 3,826,364. Nozzle 18 provides a hydrodynamically focused flow of cells within a sheath fluid, the sheath fluid and cells comprising liquid flow stream 16. As each cell or particle passes through an adjusted focused light region in flow chamber 17, where light beam 12 intersects liquid stream 16, light emitted scattered thereby may be detected. An appropriate photo diode 21 is positioned to receive light scattered forwardly by each cell or particle.

Fluorescence, if emitted by cells energized by the illumination from the light source, may also be detected. Similarly, light scattered in different directions, besides the forward direction, may be detected. In laser-excited flow cytometry 10, fluorescence and wide angle light scatter are typically collected at an angle whose viewing axis is 90° relative to the excitation axis of light beam 12. In FIG. 1, axis 24 represents the 90° viewing axis for the collection of fluorescence and wide angle scatter. Lenses 19 are placed across axis 24 to collect light passing therealong.

In order to collect fluorescence and light scatter at the 90° angle from the incident light beam, the light scatter and fluorescence is typically separated or split. This separation may be accomplished by many different techniques such as a dichroic filter or beam splitter 25. In the embodiment being described, 90° light scatter is reflected off leading face 28 of beam splitter 25, and travels along axis 31 so that it may be collected in photo multiplier tube 32. On the other hand, fluorescence is transmitted through beam splitter 25 and travels along axis 30. The fluorescence traveling along axis 30 may be further refined or separated by the provision of a dichroic mirror 34. This mirror may be used to separate the different color wavelengths in the fluorescence signal. Thus, and for example, fluorescence in the red color region may be reflected by dichroic mirror 34 along axis 35 and collected in an appropriate photo multiplier tube 36. Fluorescence in the green color region, for example, and be transmitted through dichroic mirror 34 along axis 38 and collected in an appropriate photo detector 39. Alternatively, the mirrors 25 and 34 may be beam splitters and changeable filters 37 and 40 may be used to pass the preferred wavelength and filter out those wavelengths which are not preferred. The photomultiplier tubes 32, 36 and 39 are preferably from Hamamatsu, Japan, and as model numbers R1477 or R928.

While not illustrated in FIG. 1, those skilled in the art will appreciate that various lens, filters, barrier or the like may be employed in conjunction with each of the photo multiplier tubes to obtain as pure a signal as possible. Obtaining such optically clean signals within a desired band width when a four parameter sensing apparatus (two fluorescence channels and two light scatter channels) is utilized, such as the apparatus illustrated in FIG. 1. For example an optical filter 37 or 40 may be provided between the flow chamber 17 and any photomultiplier tube 32, 36 and 39 or photodetector 21 for allowing measurement of light in any particular wavelength range.

It is preferred that, the flow cytometer 10 measures phase fluorescence lifetimes by determining phase shift between a reference signal and an emission from a particle or cell passing through its flow chamber 17. The flow chamber 17 has a passage 41 therethrough. Delivery means 42 in the flow cytometer 10 pass the stream 16 through the passage 41 so individual cells or particles 43 from a population under study are subject to modulated light from the laser beam 12. A source of intensity modulated laser light 11, 12, 13, 14 and 15 at a predetermined frequency is positioned to direct the modulated laser light to individual particles or cells 43 passing in the stream 16 through the passage 41. Detection means 21, 32, 36 and 39 responsive to emissions from individual particles or cells 43 illuminated by the source of intensity modulated laser light 11, 12, 13, 14 and 15 generates an output signal at the predetermined frequency affected by the modulation and the particle or cell. A particle 43 passing through flow chamber 17 is typically illuminated by the modulated laser light 12, 13, 14, 15 for a time of 1 to 10 micro seconds.

Figure 2:
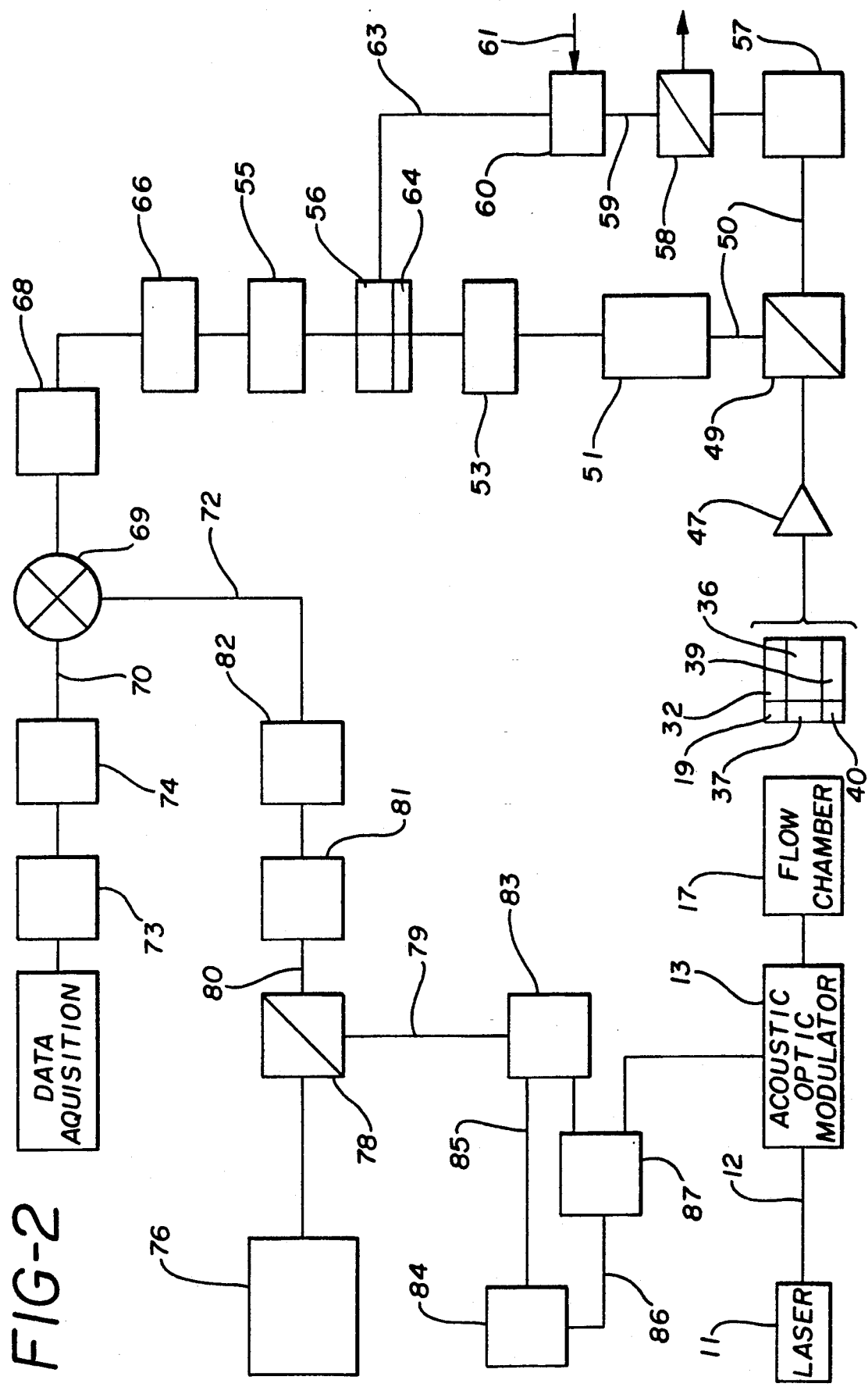
FIG. 2 is a block diagram of the preferred embodiment of the circuit for analyzing a signal to determine phase shift.
Figure 3:
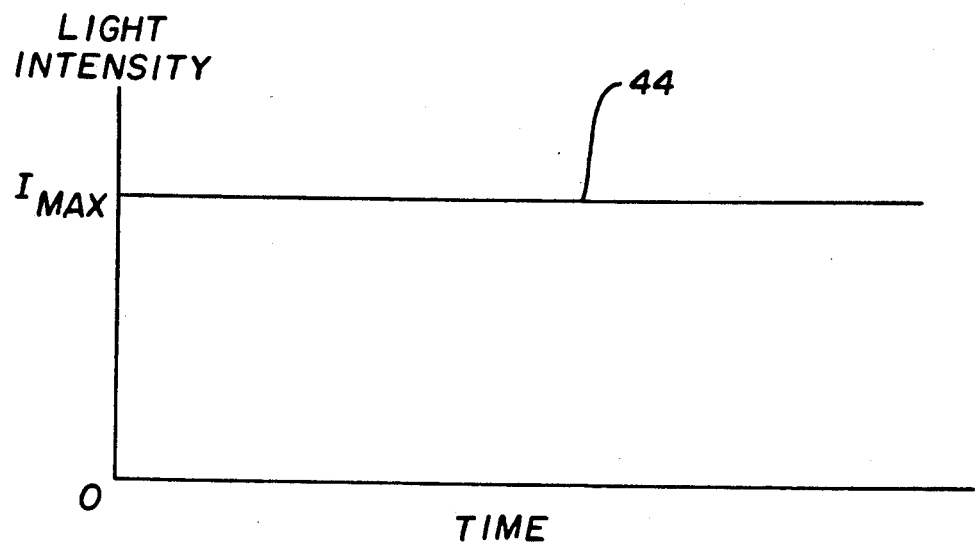
FIGS. 3-14 are graphs to show signals (wave forms) as modified by the components of the preferred embodiment.

FIG. 2 is a circuit diagram with blocks to indicate components and graphs as seen in FIG. 3 to show signals (waveforms) as modified by the components. Reference number 44 shows the laser beam 12 light intensity as constant. After passing through the acoustic optic modulator 13 the light intensity 44 as seen in FIG. 3 is:

$$I_{dif} = \alpha I_{max} \cos(\omega t)$$

wherein:

$\omega = 2\pi f$ and $f$ = frequency and $\alpha$ = conversion factor $\leq 1$ due to acoustic optic modulator 13

Figure 4:
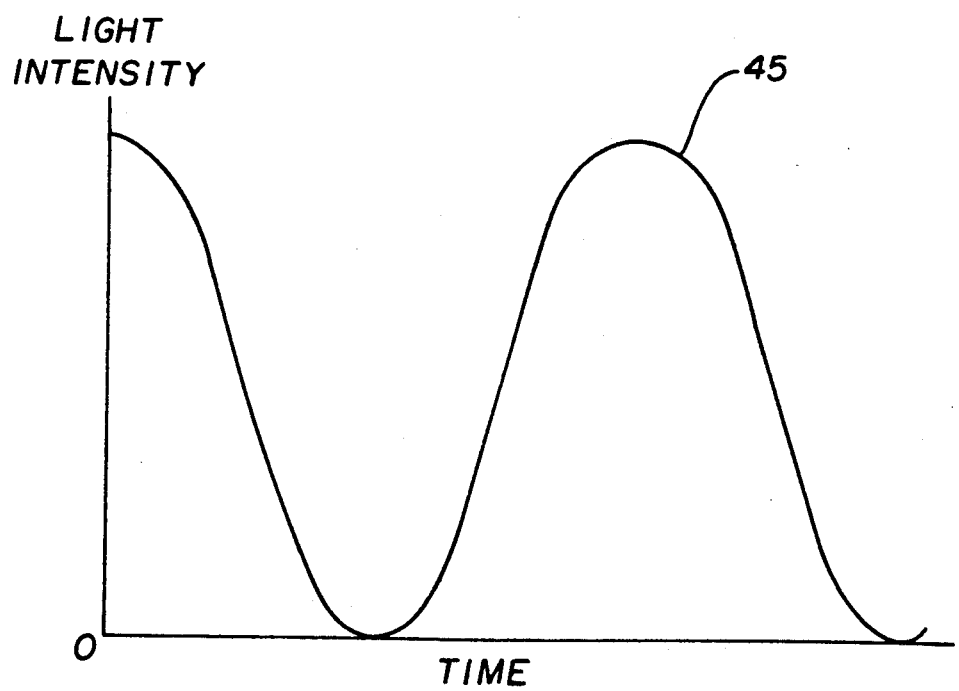

The intensity of the light beam 12 before modulation is plotted and designated as reference number 44 as shown in FIG. 3. Light beam 12 has a constant level $I_{max}$ before it is modulated by the Acoustic Optic modulator 13 and thereafter the intensity modulated signal 45 as shown in FIG. 4 is plotted. In FIG. 4, the time varying laser light intensity plot 45 is $I(t) = I_{dif}(0.5 + 0.5 \sin(\omega t))$ wherein $I_{dif}$ is some fraction of $I_{max}$ dependent on the conversion efficiency of the particular acoustic optic modulator 13. The conversion efficiency is a published specification typically greater than 75% at 30 Mhz.

Figure 5:
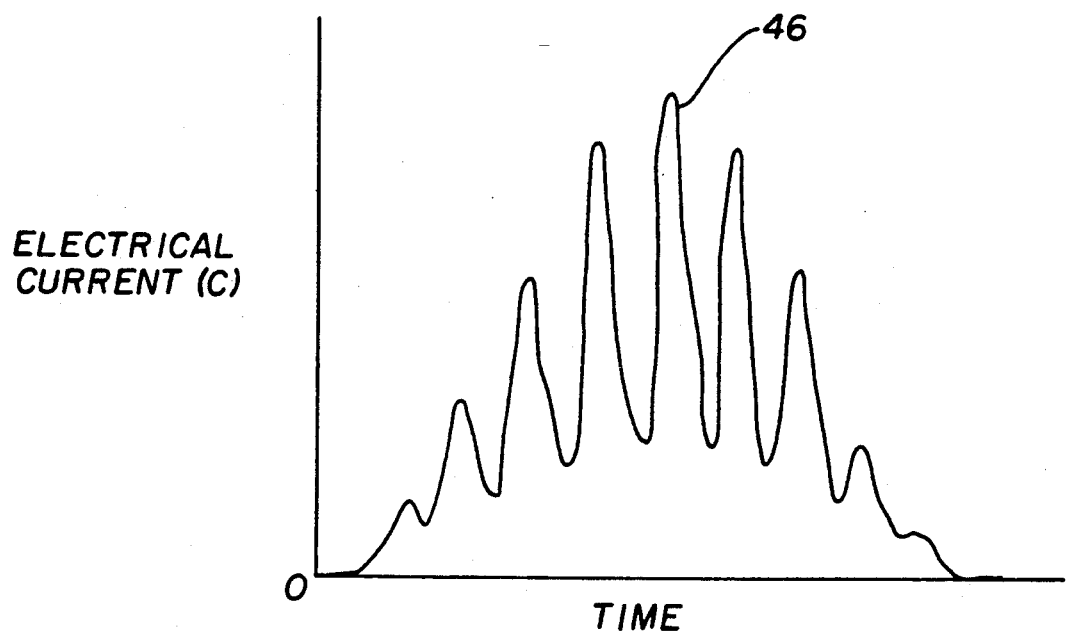

In FIG. 5 the plot 46 has signals from the photomultiple tubes 32, 36 and 39 as shown in FIG. 2 and for simplicity only one signal 46 is shown. It should be appreciated that the signals 46 are separately considered by similar methods and circuits so only one circuit is shown but several are needed or the signals must be multiplexed. Plot 46 is light scattered or emitted fluorescent light at ninety degrees to the beam 12 as detected by photomultiplier tube 32, 36, 39 as shown in FIGS. 1 and 2. If plot 46 was of the signal from photomultiplier tube 36 and was a fluorescent signal, then plot 46 would be modulated but the intensity would not return to zero during the duration of the pulse as there would be a minimum light signal with each fluctuation. The signal 46 would generally be 100% modulated for scattered light and less than 100% for fluorescent light. The depth of the modulation is the ratio of the difference of the maximum signal minus the minimum signal over or divided by the maximum signal.

Figure 6:
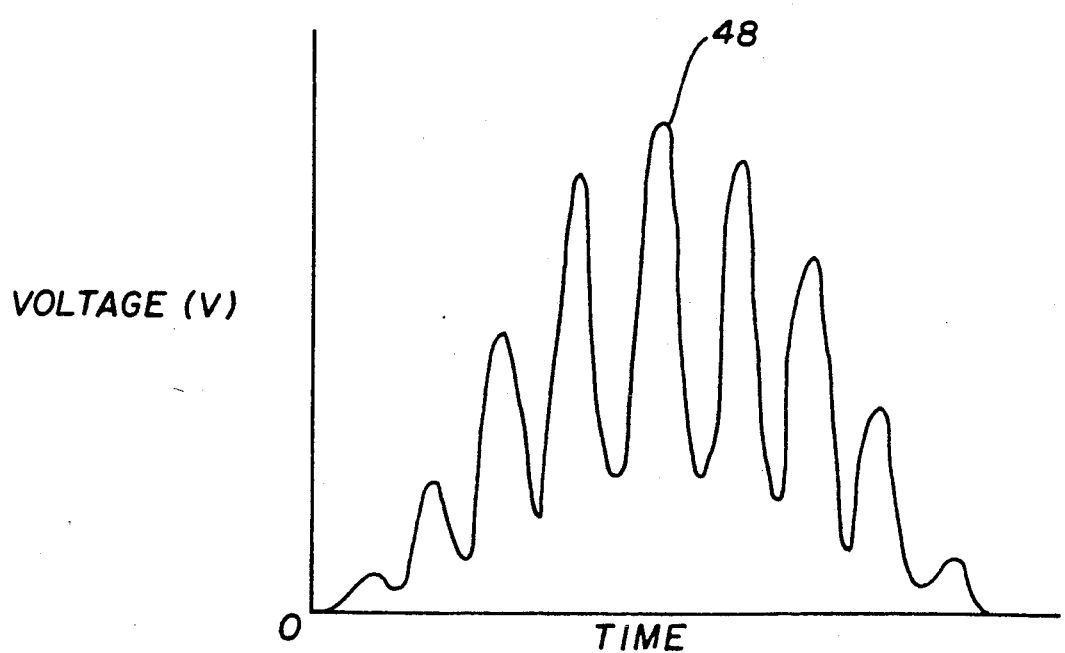

The signal plotted and labeled 46 in FIG. 5 is an electrical current which is amplified in a preamplifier 47 to convert that small output of the photomultiplier tube current to a voltage with a voltage gain of about 10. The preferred preamplifier is a model CLG140 from Comliner Corporation of Fort Collins, Colo. As shown in FIG. 6 the signal plotted at 48 is an amplified fluorescent emission and is expressed in volts. As shown in FIG. 2, a power splitter or means for dividing 49 separates the signal of plot 48 into equal signals. The two signals out of the power splitter 49 are fed into in the circuits 50 and each has the same shape as plot 48 except that each is half the power shown in plot 48. Each signal 50 is modulated at the modulation frequency and has the same amplitude and fidelity without any induced phase shift. The preferred power splitter 49 is a Model ZFRSC 2050 from Mini Circuits from New York, N.Y.

Figure 7:
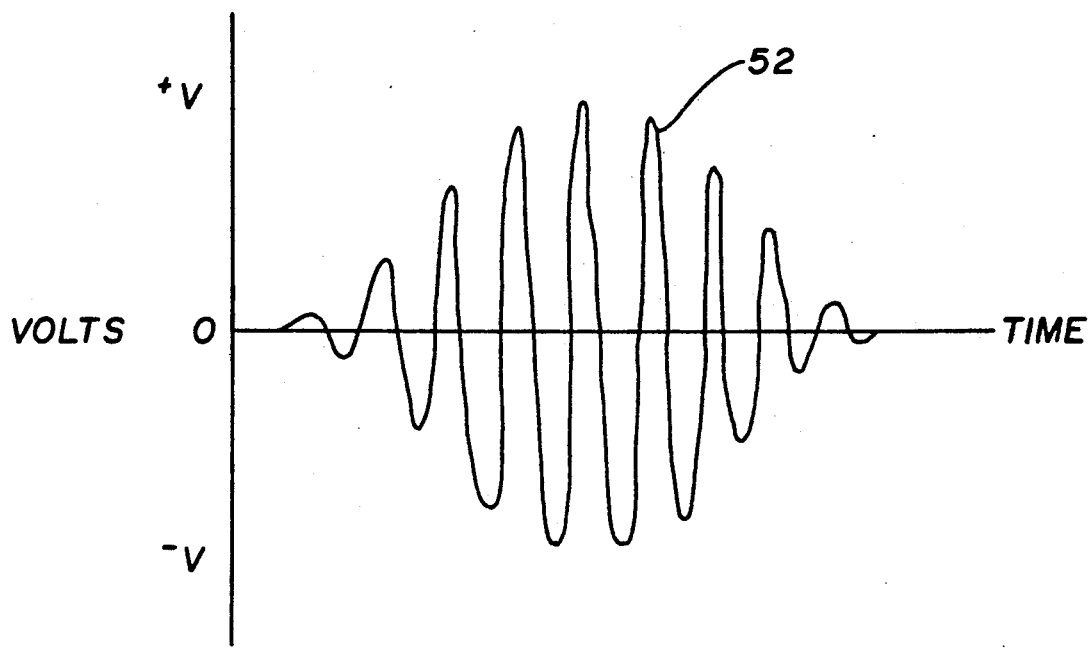
Figure 8:
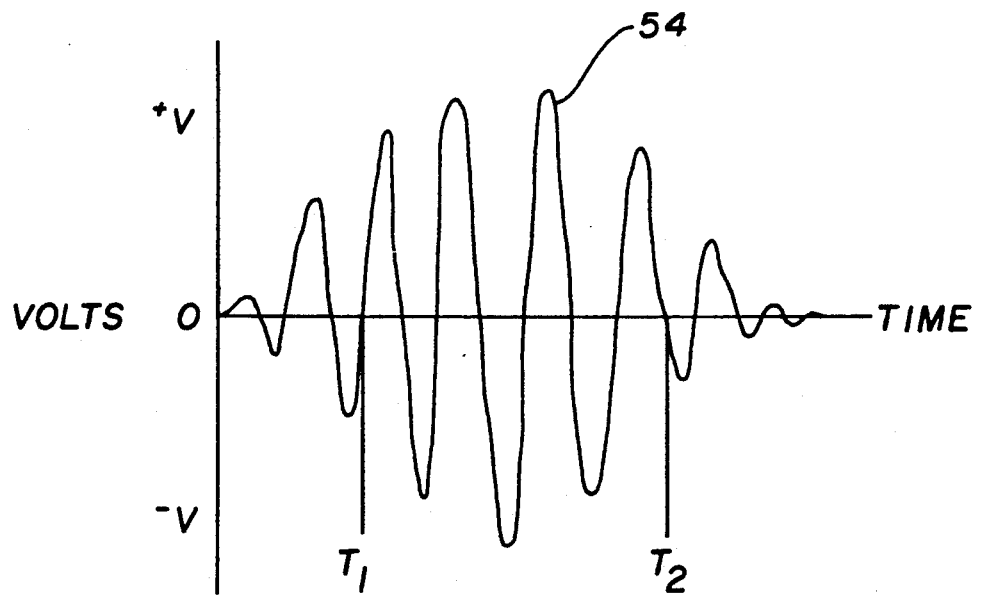

A band pass filter 51 receives and filters out of band high and low frequency signal components of one part of the divided signal 50 and produces the signal waveform plot 52 shown in FIG. 7. An attenuator 53 receives the filtered one part of the divided signals and the attenuator 53 places the filtered one part of the divided signal into an operative range by setting the minimum signal level. As shown in FIG. 8, plot 54 depicts the waveform of the minimum signal level between $T_1$ and $T_2$ as established by the attenuator 53 and band pass filter 51. A limiting circuit 55 receives and limits the attenuated and filtered one part of the divided signals 50. The preferred limiting circuit 55 is model 404–503 from Avantek of Milpitas, Calif. The timing of the signal sent to the limiting circuit 55 is shown in the space between $T_1$ and $T_2$ in plot 54.

An alternate circuit can be used to time the signal transmitted to the limiting circuit 55. A switch 56 which is responsive to a signal generated by the other part of the signal in circuit 50 from the power splitter 49, i.e. not sent to the band pass filter 51. The other part of signal 50 is filtered by a low pass filter 57 and conveyed to another power splitter 58 which like power splitter 49 divides the signal in half so that one half of the signal which goes through circuit 59 may be transmitted to a data acquisition device in order to set the timing for recording or analyzing information. The data acquisition device may be a FACScan or FACStar flow cytometry instruments of Becton Dickinson Immunocytometry Systems, San Jose, Calif. without modification to receive the signal from the power splitter as an intensity signal.

Figure 9:
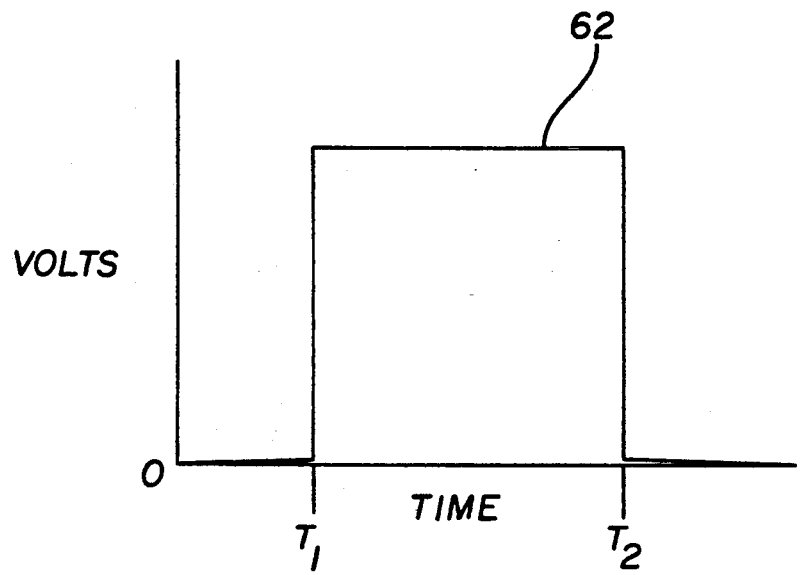

The other portion of the split signal in circuit 59 from the power splitter 58 is transmitted to a comparator 60 having separate inputs. One input is the split signal 59 and the other a reference signal 61 as shown in FIG. 9, reference signal 61 is manually preset D.C. voltage level. The comparator 60 generates a square pulse of voltage, as shown in FIG. 9, between $T_1$ and $T_2$, like that shown in signal 54. The square pulse activates the switch 56 in a timed period in a known manner. In the preferred device, switch 56 is closed by the square pulse 62. The preferred switch 56 can include a delay line 64 so that the signal passing from the attenuator 53 to the limiting circuit 55 may be time delayed such that the central most part of the signal 54 transverses switch 56 when it is closed.

It is appreciated that the phase shift, for obtaining fluorescence lifetime, may be obtained when components 57, 58, 61, 56 and 64 are removed and 53 is connected directly to 55. In addition, components 57, 58, 61, 56 and 64 are part of the circuit to enhance the signal to noise ratio when extracting phase information.

Figure 10:
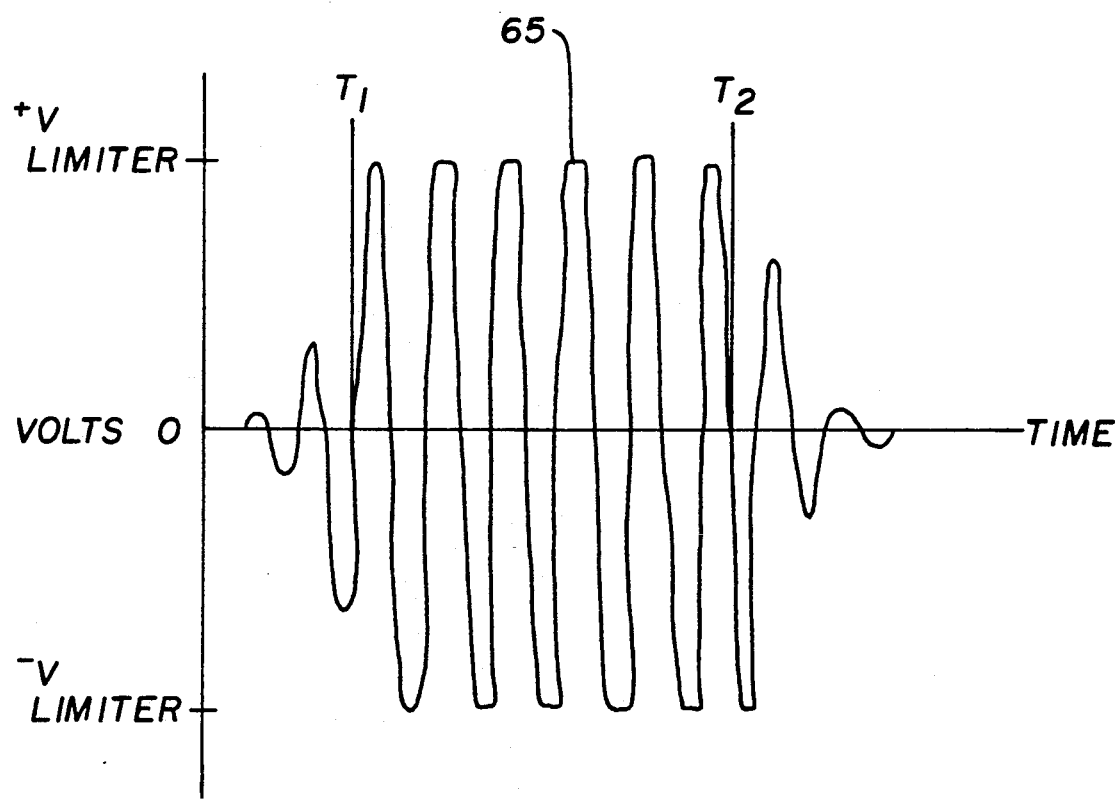

The signal from the limiting circuit 55 is shown as a limited waveform in plot 65 as best seen in FIG. 10, and is transmitted to a band pass filter 66 which in the preferred device is a model 54086 from Allan Avionics, Inc. of Minneola, N.Y. Band pass filter 66 is identical in function to the band pass filter 51 and operates in a similar fashion by removing the harmonics in the signal from the limiting circuit 55. Band pass filter 66 removes from the limited signal harmonics above the modulation frequency and an envelope below a preset level. The limiting circuit 55 has effectively eliminated all of the amplitudes above −30 dBm such that signal is set to an output level of 10 dBm and signal amplitudes below −30 dBm are increased by a gain of −40 dBm. Limiting maintains the phase characteristics of the signal as shown by the resulting waveform of plot 65. The signal peaks are squared off.

Figure 11:
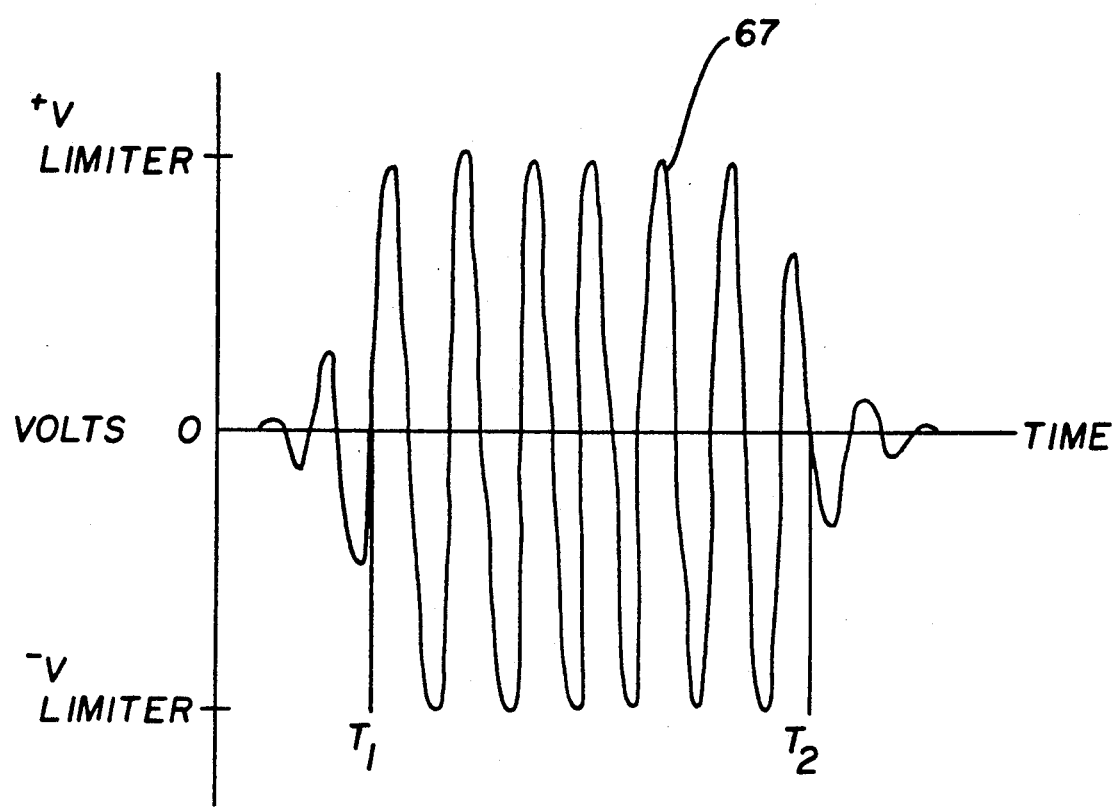

Harmonics of the main signal are created by limiting circuit 55 and band pass filter 66 removes the harmonic and reduces out of band noise. Wherefore, as shown in FIG. 11, a filtered waveform in plot 67 has the timing of the main part of the signal waveform and that is between $T_1$ and $T_2$. A variable gain amplifier 68 sets the preferred input level at 7 dBm as a first input to a double balanced mixer 69. The preferred variable gain amplifier combines a fixed gain amplifier a model ZHL 6A/BNC CAT-20, from Mini-Circuits, New York, N.Y., and an attenuator on the input to provide proper signal output level. The power level of the signals from the variable gain amplifier 68 and the second signal 72 are determined by the operating specifications of the double balanced mixer 69 which is preferably Model M-1 from Watkins Johnson of Palo Alto, Calif.

Figure 12:
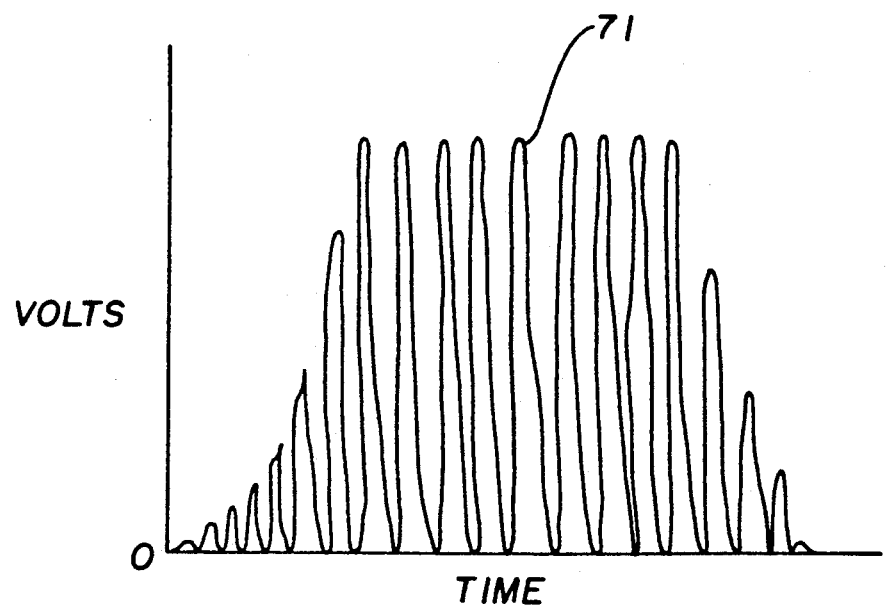

Circuits 68 and 72 are connected to the double balance mixer 69 so that a signal as shown in FIG. 12, a plot 71 may be provided in circuit 70 which in the preferred embodiment is a cable connection. Signal 71 has a duration identical to that of the pulse at or coming out of the limiting circuit 55 which is shown at 65, i.e. between $T_1$ and $T_2$. Multiplication of the signal from the variable gain amplifier 68 and the signal 72 produces the signal 71. Signal is sinusoidal and of twice the frequency as the modulation frequency shown as a waveform in plot 45 of FIG. 4. The signal in circuit 72 is multiplied in the double balance mixer 69 with the signal from variable gain amplifier 68 to generate the signal plot 71 in FIG. 12.

Figure 13:
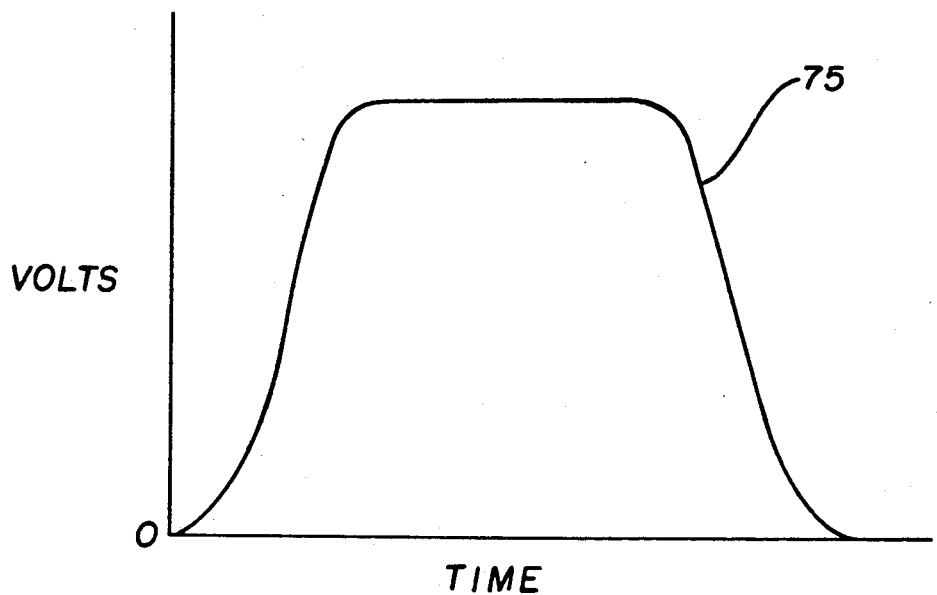

The signal of plot 71 of FIG. 12, passes through a cable 70 to a low pass filter 74 to produce a pulse as shown in FIG. 13, plot 75. The low pass filter 74 in the preferred embodiment is a Gaussian filter model VGF05P00Z from Allan Avionics, Minneola, N.Y. The absolute value of the peak voltage of the pulse in plot 75 (which could be either positive or negative) is related to the phase difference of the signals, i.e. from the variable gain amplifier 68 and the circuit 72 which are multiplied in the double balanced mixer 69. A delay line 73 is connect to a data acquisition device and the waveform of the signal transmitted to the data acquisition device is identical in form to that of plot 75 as seen in FIG. 13, but for a time shift that is adequate to properly time or synchronize the signal supplied to the data acquisition device.

Figure 14:
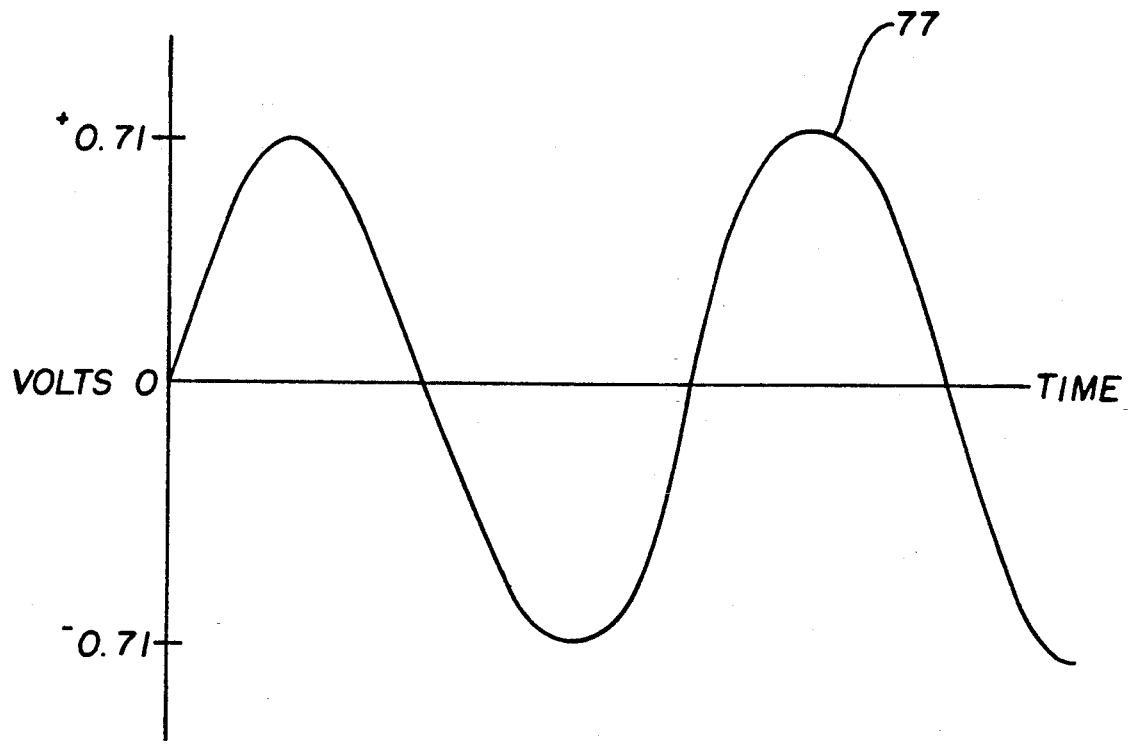

The signal in circuit 72 is generated when a frequency synthesizer 76 creates a sine wave such as shown in FIG. 14, plot 77 with a frequency between 10 Mhz and 100 Mhz at a power level of 13 dBm across a load of 50 ohms. The frequency synthesizer 76 in the preferred embodiment is a Fluke Model 6160 B. The reference signal of plot 77 is split by a power splitter 78 into two equal signals in circuits 79 and 80. Circuits 79 and 80 are used to provide the second signal 72 for the double balanced mixer 69 and the reference signal for the acoustic optic modulator 13. The preferred power splitter is a model ZFRSC 2050, from Mini Circuits, of New York, N.Y. Circuit 80 connects to a constant amplitude variable phase shifter 81. The specific phase shifter used in the preferred embodiment is a model VAR016, from Allan Avionics, Minneola, N.Y. Constant amplitude variable phase shifter 81 is designed to induce a fixed phase shift to the signal in circuit 80 and that phase shift may be somewhere in the range between 0° and 90° as set manually.

A variable gain amplifier 82 is used to give an output reference level of 7 dBm across a power load of 50 ohms to the signal in circuit 72 which is supplied to the double balance mixer 69.

The signal in circuit 79 from the power splitter 78 is supplied to a bias tee 83 which sums the D.C. voltage from 84 via 85 and the A.C. voltage from 78 via 79, in the preferred embodiment, of about $+\frac{1}{2}$ volts through circuit 85, the dc power supply 84 also supplies +26 volts through a circuit 86 to a driver 87 for the acoustic optic modulator 13. The driver 87 is interposed between the bias tee 83 and the acoustic optic modulator 13 such that a standing sine wave is generated in the acoustic optic modulator 13 due to the input from the 200 Mhz driver 87. The acoustic optic modulator driver 87 is in the preferred embodiment Model 1200 from Crystal Technology of Palo Alto, Calif.

Phase shift measurements are directly a function of the plot 75 as shown in FIG. 13 and are fed to the data acquisition device which includes means for correlating the measured phase shift to characteristics of the cells or particles passing through the flow chamber 17 of the flow cytometer 10. Sorting means may be provided to receive the cells or particles and segregate them on the basis of fluorescent lifetimes as determined by phase shift.

A method of measuring in a flow cytometer phase fluorescence lifetimes of cells or particles marked with one or more fluorescent markers has the step of passing individual cells or particles in a flow stream through a flow chamber 17 in a flow cytometer 10, exciting each cell or particle 43 passing through the flow chamber 17 with modulated laser light as in plot 45. In another step in the method, the modulated laser light is of a wavelength that stimulates at least one of the markers with modulated laser light at a predetermined modulation frequency. Detecting the stimulated fluorescent emissions from the flow chamber 17 for each cell or particle 43 to produce an output signal representative of the detected stimulated emissions is a further step. The steps of analyzing the output signal includes dividing the output signal representative of the detected emissions into two equal signals one of which is filtered in a band pass filter. The divided and filtered signal is amplified for transmission to the limiting circuit 55 which produces a limited signal and sends the limited signal to the double balance mixer 69.

That limited signal is multiplied with a reference signal in the double balance mixer 69 to produce a multiple signal. The multiple signal is filtered with the low pass filter 74 to produce a peak signal. The peak signal is related to the phase shift of the fluorescent emission relative to a reference signal. The method has the additional step of modulating the laser light with the acoustic optic modulator 13. The additional step of obtaining the reference signal from the modulated laser light may be a part of the method. The additional step of correlating the measured phase shift to a characteristic of the cells or particles in the stream passing through the flow chamber 17 of the flow cytometer 10 may be a part of the method. The cells or particles can be sorted on the basis of fluorescent lifetimes as determined by phase shift.

What is claimed is:

1. An instrument to measure phase fluorescence lifetimes of signals representative of characteristics of subpopulations of particles by determining phase shift between a reference signal and emissions from the particles, the instrument comprising:

delivery means for moving particles through an interrogation window of the instrument;

a source of modulated light at a predetermined frequency, the source positioned to direct and focus the modulated light onto individual particles in the window;

detection means responsive to emissions from the individual particles illuminated by the source of modulated light, the detection means for generating an output signal:

means for filtering the output signal and producing a filtered signal thereby passing a frequency band centered at the modulation frequency:

an amplifier for setting the signal level above a preset level thereby producing a filtered, amplified signal;

a limiting circuit to limit the filtered, amplified signal thereby producing a limited signal;

a filter to remove from the limited signal, harmonics above the modulation frequency and an envelope below a preset frequency thereby producing a filtered limited signal, and a mixer to mix the filtered limited signal with a reference signal thereby relating the reference signal and the filtered limited signal to determine the relative phase shift of the fluorescence emissions.

2. A flow cytometer operative to simultaneously measure phase fluorescence lifetimes of multiple particles by determining phase shift between a reference signal and emissions from the particles as the particles pass therethrough comprising:

delivery means for establishing a stream of particles of multiple populations to pass through a passage in a flow chamber of a flow cytometer;

a source of modulated light at a predetermined frequency, the source positioned to direct and focus the modulated light onto individual particles passing in the stream through the passage;

detection means responsive to emissions from the individual particles or cells illuminated by the source of modulated light, the detection means for generating an output signal pulse at the predetermined frequency;

means for dividing the output signal pulse into signal pulses, each divided signal pulse being modulated at the modulation frequency and having substantially the same amplitude and fidelity without any induced phase shift;

means for filtering the output signal pulse thereby passing a frequency band centered at the modulation frequency and with a band width approximately equal to the frequency band width of the envelope of the output signal pulse;

means responsive to a timing circuit for permitting the central part of the filtered signal to pass, the means responsive including a switch responsive to a low frequency portion of the other part of the equally divided signal;

a comparator for controlling the switch by comparing the portion of the low frequency signal and a reference;

a limiting circuit to receive and limit the second part of the divided signal;

a filter to receive the limited signal and remove harmonics above the modulation frequency and the envelope below a preset frequency, and a double balanced mixer to multiply the limited signal with a reference signal and produce a multiple signal for relating the reference signal and the filtered limited signal and for determining the relative phase shift of the fluorescence emissions.

3. The flow cytometer of claim 1 further comprising an acoustic optic modulator to modulate the laser light from the source.

4. The flow cytometer of claim 3 further comprising a reference oscillator for driving the acoustic optic modulator to produce the reference signal used in the double balanced mixer.

5. The flow cytometer of claim 3 wherein the acoustic optic modulator has circuitry which produces an intensity modulated signal.

6. The flow cytometer of claim 2 wherein the comparator is connected to transmit only the central portion of the signal.

7. The flow cytometer of claim 6 wherein sorting means receive the cells or particles and segregate them on the basis of fluorescent lifetimes as determined by phase shift.

8. A method of measuring in a flow cytometer phase fluorescence lifetimes of particles having one or more fluorescent markers comprising:

passing individual particles in a flow stream through a flow chamber in a flow cytometer;

exciting each particle passing through the flow chamber with modulated light of a wavelength that stimulates at least one of the markers, the modulated light being at a predetermined modulation frequency;

detecting the stimulated fluorescent emissions from the flow chamber for each cell or particle;

producing an output signal representative of the detected stimulated emissions;

filtering and limiting the output signal to obtain a filtered limited signal;

mixing the filtered limited signal with a reference signal, and relating the reference signal and the filtered limited signal to determine the relative phase shift of the fluorescence emissions.

9. The method of claim 8 with the additional step of obtaining the reference signal from a reference oscillator used to drive the modulator.

10. The method of claim 9 wherein the modulator generates sinusoidal modulation wave.

11. The method of claim 8 with the additional step of correlating the measured phase shift to a characteristic of the cells or particles in the stream passing through the flow chamber of the flow cytometer.

12. The method of claim 8 with the further step of sorting cells or particles on the basis of fluorescent lifetimes as determined by phase shift.

13. An instrument operative in a dynamic system to simultaneously measure phase fluorescence lifetimes of pulsing signals representative of characteristics of subpopulations of cells or particles by determining phase shift between a reference signal and emissions from particles or cells comprising:

delivery means for moving particles or cells of multiple populations to pass through an interrogation window of the instrument;

a source of intensity modulated laser light at a predetermined frequency, the source positioned to direct and focus the modulated laser light onto individual particles or cells in the window;

detection means responsive to emissions from the individual particles or cells illuminated by the source of intensity modulated laser light, the detection means for generating an output signal pulse at the predetermined frequency;

means for dividing the output signal pulse into equal signals, each equal signal being modulated at the modulation frequency and having the same amplitude and fidelity without any induced phase shift;

means for filtering one part of the equally divided signal thereby passing a frequency band centered at the modulation frequency and with a band width approximately equal to the frequency band width of the envelope of the one part signal pulse;

a variable amplifier for setting the signal level above a preset level;

a limiting circuit to limit the filtered amplified one part of the equally divided signal;

a filter to remove from the limited signal harmonics above the modulation frequency and an envelope below a preset frequency;

means to determine the amplitude and/or width of the other part of the equally divided signal; and a double balance mixer to multiply the filtered limited signal with a reference signal and produce a multiple signal thereby relating the reference signal and the filtered limited signal to determine the relative phase shift of the fluorescence emissions.

14. A device for measuring phase fluorescence of a particle, the device comprising:

means for producing a light beam;

modulating means for modulating the light beam;

means for passing the particle through the light beam such that the particle emits fluorescence;

detection means for detecting the fluorescence emitted by the particle and for producing a signal in response to the fluorescence emitted by the particle;

means for producing a reference signal;

means for mixing the signal in response to the fluorescence and the reference signal to determine the difference in phase between the signal in response to the fluorescence and the reference signal.

15. The device of claim 14 wherein the modulating means generates a modulating wave at a modulating frequency.

16. The device of claim 15 wherein the modulating wave provides the reference signal.

17. The device of claim 14 wherein the means for determining the difference in phase comprises means for mixing the signal in response to the fluorescence emitted by the particle and the reference signal.

18. The device of claim 14 further comprising means for processing the signal in response to the fluorescence emitted by the particle, the means for processing comprising a band pass filter.

19. The device of claim 18 wherein the means for processing further comprises an attenuator.

20. The device of claim 15 wherein the modulating means comprises a frequency synthesizer and an opto-acoustic modulator driven by the frequency synthesizer.

21. The device of claim 17 wherein the means for determining the difference in phase comprises a double balanced mixer.

* * * * *